(12) United States Patent
Klein et al.

(10) Patent No.: US 10,987,201 B2
(45) Date of Patent: Apr. 27, 2021

(54) DENTAL IMPLANT

(71) Applicant: PALTOP ADVANCED DENTAL SOLUTIONS LTD., Caesarea (IL)

(72) Inventors: Michael Klein, Maale Adumim (IL); Mordechai Mor Mills, Pardesiya (IL); Shlomo Hillel, Petach Tiqva (IL)

(73) Assignee: PALTOP ADVANCED DENTAL SOLUTIONS LTD., Caesarea (IL)

( * ) Notice: Subject to any disclaimer, the term of this patent is extended or adjusted under 35 U.S.C. 154(b) by 0 days.

(21) Appl. No.: 15/440,462

(22) Filed: Feb. 23, 2017

(65) Prior Publication Data

US 2017/0239021 A1 Aug. 24, 2017

Related U.S. Application Data

(60) Provisional application No. 62/298,593, filed on Feb. 23, 2016.

(51) Int. Cl.
*A61C 8/00* (2006.01)
*A61B 6/14* (2006.01)
*A61C 13/225* (2006.01)

(52) U.S. Cl.
CPC .............. *A61C 8/0077* (2013.01); *A61B 6/14* (2013.01); *A61C 8/0022* (2013.01);
(Continued)

(58) Field of Classification Search
CPC ... A61C 8/0077; A61C 8/0075; A61C 8/0078; A61C 8/0022; A61C 8/0037; A61C 13/225; A61B 6/14
(Continued)

(56) References Cited

U.S. PATENT DOCUMENTS 4,468,200 A * 8/1984 Munch ................. A61C 8/0022
433/174
4,738,623 A 4/1988 Driskell
(Continued)

FOREIGN PATENT DOCUMENTS

WO 2000/032134 6/2000
WO 2010/025191 3/2010

OTHER PUBLICATIONS

Do Nascimento, Cassie, and Rubens Ferreira de Albuquerque Jr. "Bacterial leakage along the implant-abutment interface." Implant Dentistry—The Most Promising Discipline of Dentistry. InTech, 2011.

(Continued)

*Primary Examiner* — Matthew M Nelson
(74) *Attorney, Agent, or Firm* — Sughrue Mion, PLLC

(57) ABSTRACT

A dental implant having a central longitudinal axis at a bone-entry portion thereof is provided. The dental implant includes a threaded elongate fixture, at the bone-entry portion of the dental implant, shaped and sized for insertion into a bone of a subject, and a non-threaded emergence collar coronal to the fixture and smoother than the fixture. The emergence collar has a non-circular cross-section at least in a plane that is at least 1 millimeter coronal to the fixture and that is perpendicular to the longitudinal axis, the emergence collar and the fixture being formed of, and adjacently disposed along, a single piece of metal. Other applications are also described.

13 Claims, 6 Drawing Sheets

(52) U.S. Cl.
CPC .......... *A61C 8/0037* (2013.01); *A61C 8/0075* (2013.01); *A61C 8/0078* (2013.01); *A61C 13/225* (2013.01)

(58) Field of Classification Search
USPC .................................................. 433/172–176
See application file for complete search history.

(56) References Cited

U.S. PATENT DOCUMENTS

| | | | |
|---|---|---|---|
| 5,000,686 | A | 3/1991 | Lazzara et al. |
| 5,092,771 | A | 3/1992 | Tatum |
| 5,813,858 | A | 9/1998 | Singer |
| 5,871,486 | A | 2/1999 | Huebner et al. |
| 5,897,319 | A | 4/1999 | Wagner et al. |
| 6,062,856 | A | 5/2000 | Sussman |
| 6,174,167 | B1 | 1/2001 | Wohrle |
| 6,283,754 | B1* | 9/2001 | Wohrle ................ A61C 8/0012 433/173 |
| 6,342,057 | B1 | 1/2002 | Brace et al. |
| 7,597,557 | B2 | 10/2009 | Fromovich et al. |
| 7,677,891 | B2 | 3/2010 | Niznick |
| 8,021,154 | B2 | 9/2011 | Holzner et al. |
| 8,087,935 | B2 | 1/2012 | Beaty et al. |
| 8,197,255 | B2 | 6/2012 | Fromovich et al. |
| 8,483,857 | B2 | 7/2013 | Orth |
| 8,714,977 | B2 | 5/2014 | Fromovich et al. |
| 8,899,984 | B2 | 12/2014 | Llop et al. |
| 8,968,002 | B2 | 3/2015 | Purga et al. |
| 9,011,146 | B2 | 4/2015 | Suttin et al. |
| 2003/0061679 | A1 | 4/2003 | Chang et al. |
| 2005/0100863 | A1 | 5/2005 | Chang |
| 2006/0121410 | A1 | 6/2006 | Aravena |
| 2006/0147880 | A1 | 7/2006 | Krumsiek et al. |
| 2008/0119895 | A1 | 5/2008 | Manceau |
| 2009/0202959 | A1 | 8/2009 | Ajlouni et al. |
| 2012/0237898 | A1 | 9/2012 | Palti et al. |
| 2012/0237899 | A1* | 9/2012 | Holmstrom .......... A61C 8/0001 433/174 |
| 2012/0295225 | A1 | 11/2012 | Fromovich et al. |
| 2013/0089834 | A1 | 4/2013 | Fromovich et al. |
| 2013/0095451 | A1* | 4/2013 | Menzel ................ A61C 8/0018 433/173 |
| 2013/0203018 | A1 | 8/2013 | Marotta |
| 2013/0209956 | A1 | 8/2013 | Sanders |
| 2013/0316306 | A1 | 11/2013 | Carden et al. |
| 2014/0106305 | A1* | 4/2014 | Jacoby ................ A61C 8/0006 433/174 |
| 2014/0205970 | A1* | 7/2014 | Courvoisier ........... A61C 8/005 433/174 |
| 2014/0242545 | A1 | 8/2014 | Brun |
| 2014/0377718 | A1 | 12/2014 | Korten et al. |
| 2015/0056573 | A1* | 2/2015 | Collins ................ A61C 8/0012 433/174 |
| 2015/0125822 | A1 | 5/2015 | Cramer Von Clausbruch |
| 2015/0230896 | A1 | 8/2015 | Korten et al. |
| 2015/0351878 | A1 | 12/2015 | Honig |
| 2016/0015483 | A1* | 1/2016 | Kumar ................ A61C 8/0012 606/301 |
| 2016/0062346 | A1* | 3/2016 | Akmakjian ........ A61C 13/0004 700/98 |
| 2016/0081771 | A1 | 3/2016 | Fromovich et al. |
| 2016/0128811 | A1 | 5/2016 | Rauh et al. |
| 2016/0213452 | A1* | 7/2016 | Simmons, Jr. ....... A61C 8/0077 |
| 2017/0007375 | A9* | 1/2017 | Fromovich .......... A61C 8/0022 |

OTHER PUBLICATIONS

Sahiwal, Indira G., et al. "Macro design morphology of endoseous dental implants." The Journal of prosthetic dentistry 87.5 (2002): 543-551.
Eraslan, Oğuz, and Özgür İnan. "The effect of thread design on stress distribution in a solid screw implant: a 3D finite element analysis." Clinical oral investigations 14.4 (2010): 411-416.
U.S. Appl. No. 62/298,593, filed Feb. 23, 2016.

* cited by examiner

DENTAL IMPLANT

CROSS-REFERENCES TO RELATED APPLICATIONS

The present application claims priority from U.S. Provisional Application 62/298,593 to Klein et al., entitled "Dental Implant," filed Feb. 23, 2016.

FIELD OF THE APPLICATION

Applications of the present invention relate generally to prosthetics and more specifically to dental implants.

BACKGROUND OF THE APPLICATION

Dental implants typically are implanted as one of three components: the implant fixture which is placed in bone, and which is connected to an abutment. The abutment in turn secures a dental prosthesis, e.g., a crown.

The implant fixture is typically a metal (e.g., titanium) cylindrical and/or screw-shaped structure that is used to replace a missing tooth root by implantation into a jawbone of a subject. The implant fixture undergoes osseointegration with the bone in which it is implanted and functions as an artificial tooth root. The implant fixture may vary in length, diameter, and thread pattern. The surface of the implant fixture is typically treated during manufacture in order to roughen the surface to maximize contact between the implant and the bone, improve stability, and enlarge implant surface area.

The abutment is typically a connecting element which is placed on (i.e., coupled to) the coronal portion of the implant fixture subsequently to implantation of the implant fixture into the bone. The abutment is inserted into an opening at the coronal portion of the implant fixture and when in place passes from the implant, through the gum of the subject. Some dental implants comprise a one-piece dental implant having a combined implant fixture and abutment. The abutment in the one-piece dental implant is typically a standard metallic collar which protrudes through the gum while the implant fixture undergoes osseointegration into the jawbone.

The dental prosthesis is an intra-oral prosthesis, e.g., a tooth (crown) or teeth (bridge, denture), which is coupled to the abutment and is supported by the implanted implant fixture.

SUMMARY OF APPLICATIONS

Some applications of the present invention provide a dental implant comprising a combined implant fixture and a customized emergence collar, the fixture and customized emergence collar being formed of, and adjacently disposed along, a single piece of metal.

The fixture typically comprises a threaded elongate structure which forms a portion of the implant, and which is shaped and sized for insertion into the bone of the subject during implantation of the implant. The fixture subsequently undergoes osseointegration with the bone to serve as an artificial tooth root. The customized emergence collar is disposed coronal to the fixture and comprises a non-threaded, typically smooth portion, which is typically smoother than the fixture. The customized emergence collar is shaped and sized such that it may protrude through oral soft tissue of the subject when the fixture is implanted in the bone.

In accordance with some applications of the present invention, the customized emergence collar is generated based on CT scan data and/or intra-oral scan data of the subject. The customized emergence collar is shaped and sized based on the scan data to shape the subject's anatomy (e.g., soft tissue) and to provide enhanced gum healing and gum shape around the customized emergence collar. Additionally, the customized emergence collar is shaped and sized based on the scan data to provide an esthetic placement of the dental crown on an abutment (which is placed on the customized emergence collar), such that the crown is properly aligned with the dental arch of the subject and the subject's other teeth. Typically, due to generating the customized emergence collar based on the scan data, the customized emergence collar has a non-circular cross-section at least in a plane that is at least 1 millimeter coronal to the fixture and that is perpendicular to a central longitudinal axis of the fixture.

In the context of the present application and in the claims, the term "coronal" refers to the direction towards the dental crown that is eventually placed on the dental implant, as opposed to "apical," which refers to the direction towards the apex of the fixture.

There is therefore provided in accordance with some applications of the present invention a dental implant having a central longitudinal axis at a bone-entry portion thereof, and including:

a threaded elongate fixture, at the bone-entry portion of the dental implant, shaped and sized for insertion into a bone of a subject; and a non-threaded emergence collar coronal to the fixture and smoother than the fixture, the emergence collar having a non-circular cross-section at least in a plane that is at least 1 millimeter coronal to the fixture and that is perpendicular to the longitudinal axis, the emergence collar and the fixture being formed of, and adjacently disposed along, a single piece of metal.

For some applications, the emergence collar is formed by using intra-oral scan and CT scan data of the subject, and the emergence collar is shaped and sized for insertion into oral soft tissue of the subject based on the scan data.

For some applications, the dental implant further includes an abutment configured to be coupled to the emergence collar such that a central longitudinal axis of the abutment is not collinear with the central longitudinal axis of the dental implant.

For some applications, the dental implant further includes a dental crown configured to be coupled to the abutment.

For some applications, the fixture has a length of 6-20 mm.

For some applications, the fixture has a diameter at a largest threaded portion of the fixture that is 2-9 mm.

There is therefore provided in accordance with some applications of the present invention a method for generating a dental implant having a fixture and an emergence collar, the method including:

receiving data from a CT scan and an intra-oral scan of a subject; and forming, along a single piece of metal, a non-threaded emergence collar based on the CT and intra-oral scan data, the emergence collar being disposed coronal to the fixture of the dental implant.

For some applications, (a) the method includes receiving the fixture as a non-customized threaded fixture, a blank portion being disposed coronally to the non-customized threaded fixture, and (b) forming the non-threaded emergence collar includes forming the non-threaded emergence collar along the blank portion.

For some applications, receiving the fixture includes receiving the fixture prior to receiving the data.

For some applications, the method further includes implanting the dental implant in a subject's mouth such that the fixture is positioned in bone and the emergence collar is positioned in soft tissue of the subject.

For some applications, the method further includes placing an abutment on the emergence collar such that a central longitudinal axis of the abutment is not collinear with a central longitudinal axis of the dental implant.

For some applications, the method further includes placing a dental crown on the abutment.

For some applications, placing the abutment does not include providing a step of removing a healing abutment and placing a permanent abutment.

For some applications, placing the abutment includes placing the abutment such that the interface between the emergence collar and the abutment is located at a soft tissue level.

The present invention will be more fully understood from the following detailed description of applications thereof, taken together with the drawings, in which:

DETAILED DESCRIPTION OF APPLICATIONS

Figure 4:
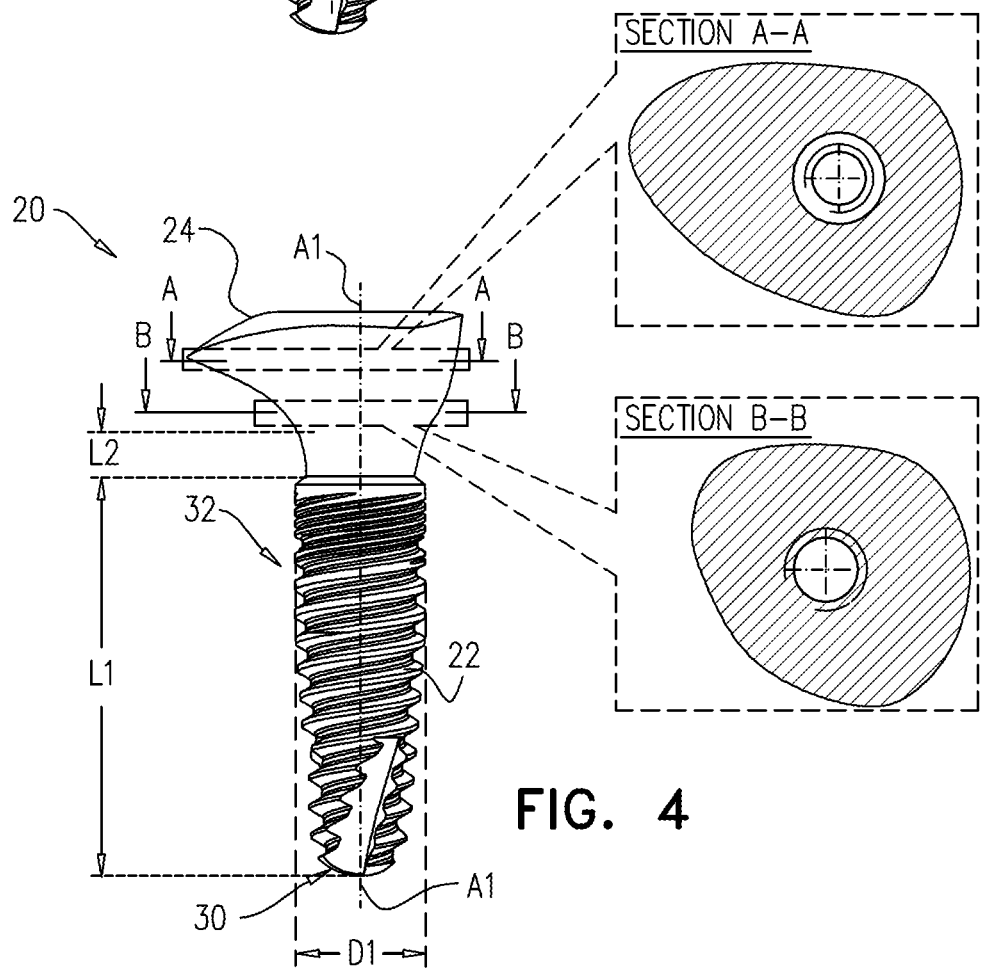
FIG. 4 is a schematic illustration of the dental implant in accordance with some applications of the present invention.
Figure 5:
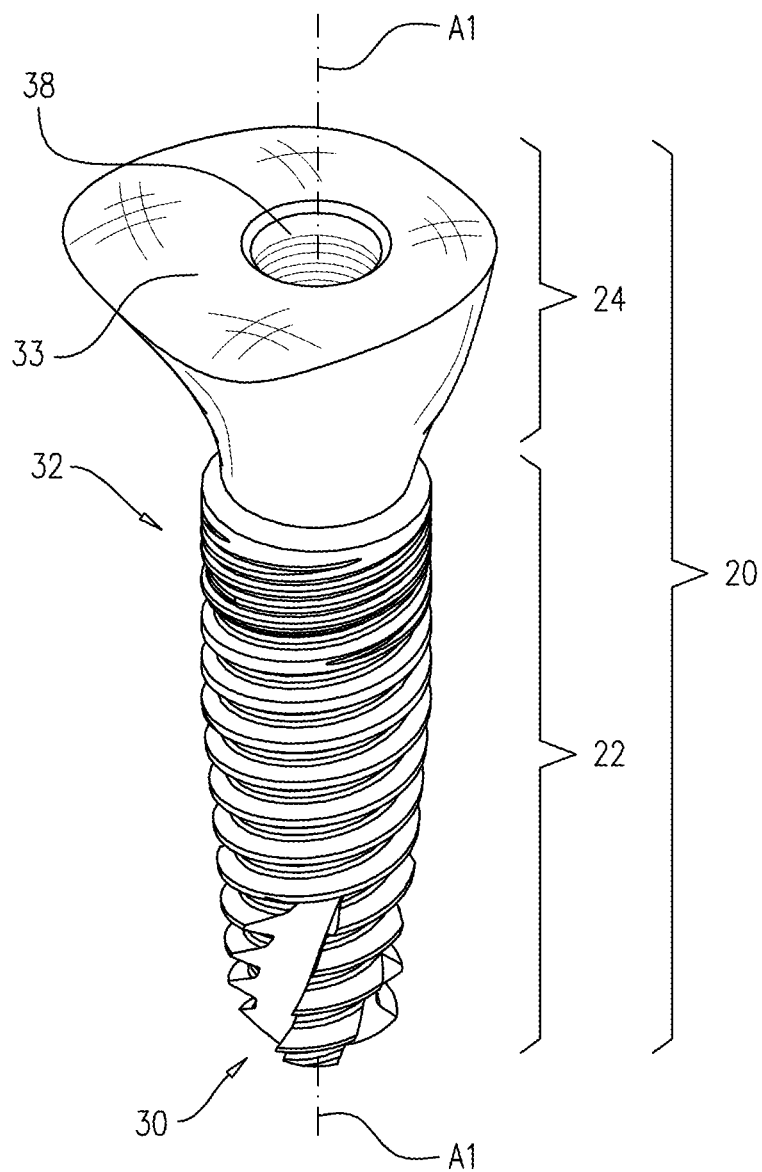
FIG. 5 is a schematic illustration of an additional view of the dental implant, in accordance with some applications of the present invention.

The present detailed description begins with a description of an implant 20 as depicted in FIGS. 4 and 5.

Implant 20 comprises a combined implant fixture 22 and a customized emergence collar 24. Fixture 22 and customized emergence collar 24 are formed of, and adjacently disposed along, a single piece of metal.

Fixture 22 typically comprises an elongate threaded structure which is shaped and sized for entry into a bone, e.g., a jawbone of the subject, during implantation of the dental implant. Following implantation, fixture 22 undergoes osseointegration and fuses with the bone to function as a prosthetic tooth root. Fixture 22 is shaped to define an apical portion 30 at an apical end (i.e., distal with respect to the physician) of the fixture and a coronal portion 32 at a coronal end (i.e., proximal with respect to the physician) of the fixture.

As shown in FIGS. 4 and 5, customized emergence collar 24 is adjacent to, and disposed coronal to, coronal portion 32 of fixture 22. Customized emergence collar 24 is typically non-threaded, and has a surface that is smoother than a surface of fixture 22, typically being polished during manufacture. Customized emergence collar 24 is shaped and sized such that it protrudes at least in part into oral soft tissue of the subject when fixture 22 is implanted in the bone, as described hereinbelow with reference to FIG. 6A.

Fixture 22 of implant 20 typically has standard dimensions for fixtures that are known in the art of implantology. For example, a length L1 of the fixture may be at least 6 mm and/or less than 20 mm (e.g., 6-16 mm), and a diameter D1 of the fixture at the largest threaded portion thereof may be at least 2 mm and/or less than 9 mm.

Typically, using an implant 20 having customized emergence collar 24 provides improved subsequent abutment and crown positioning, resulting in enhanced esthetic and functional results (e.g., improved gum healing and shaping). For example, in cases of insufficient bone due to bone loss, it is difficult or impossible for a surgeon to place a fixture in a position that Provides proper esthetic alignment of the crown with the other teeth, when the center of the abutment-crown interface is located directly coronal to the fixture (i.e., along the central longitudinal axis of the fixture). To address this issue, implant 20 having customized emergence collar 24 provides an improved emergence profile into the gum, promoting both healthy healing of the gum, shape of the gum, and proper marginal fitting of the crown on the abutment such that the crown is aligned with the existing teeth of the subject. Placing the abutment and the crown is typically performed in one or two separate procedures following implantation of implant 20.

Customized emergence collar 24 is typically customized based on CT scan data and/or intra-oral scan data of the subject. CT scan data and/or intra-oral scan data of the subject are obtained, and customized emergence collar 24 is then shaped and sized based on the scan data to allow suitable abutment and crown positioning and gum shape for the subject. Since customized emergence collar 24 is customized based on the scan data, it typically provides improved gum healing and gum shaping around the customized emergence collar and provides esthetic placement of the dental crown on an abutment such that the crown is properly aligned with the dental arch of the subject and the other teeth of the subject. Since customized emergence collar 24 is customized for the subject, customized emergence collar 24 typically has a non-circular cross-section at least in a plane that is at least at a length L2, e.g., at least 1 millimeter, coronal to fixture 22 and that is perpendicular to a central longitudinal axis A1 of fixture 22, as shown in FIG. 4. Sections A-A and B-B of FIG. 4 show that the non-circular cross-section may vary in shape (and not only in size) along the length of customized emergence collar 24.

As shown in FIG. 5, customized emergence collar 24 is typically shaped to define a screw access hole 38 at a coronal end of customized emergence collar 24 that is directly aligned with central longitudinal axis A1 of fixture 22.

In the context of the present application and in the claims, the central longitudinal axis of the fixture refers to the central longitudinal axis of the shank of the threaded portion of the fixture, excluding the threading of the fixture.

As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

Figure 2:
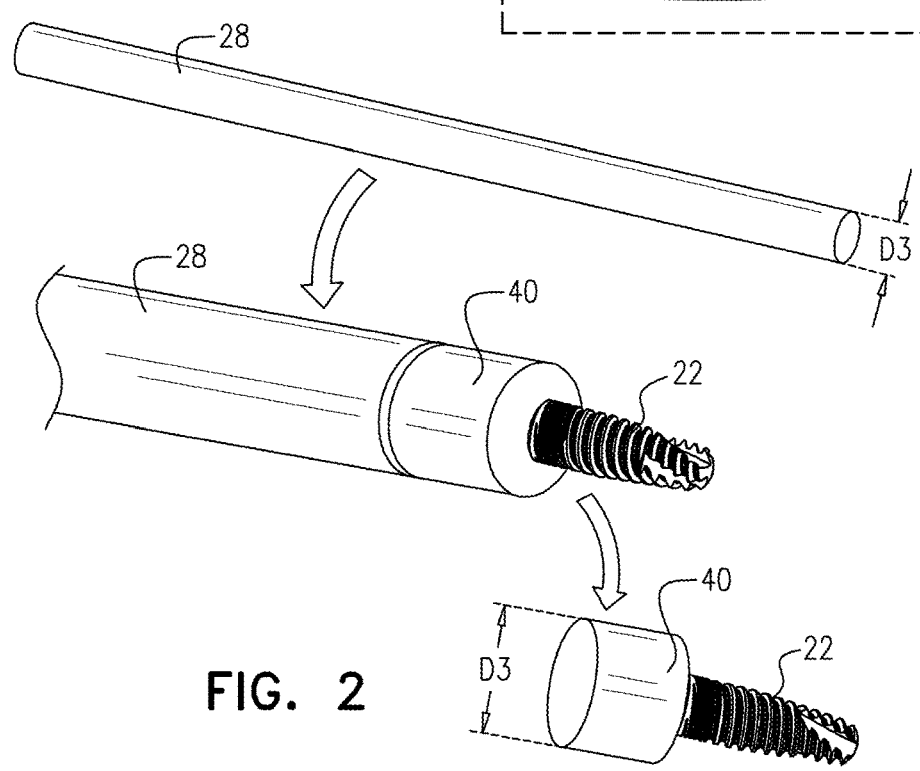
FIG. 2 is a schematic illustration of a single piece of metal from which the dental implant is formed, and a stage in the manufacturing of the dental implant from the single piece of metal, in accordance with some applications of the present invention.
Figure 3:
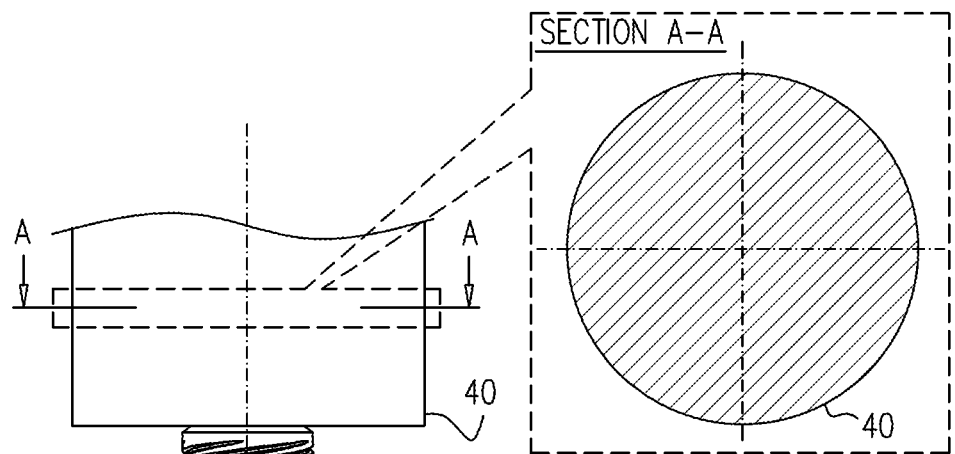
FIG. 3 is a schematic illustration of an additional view of the stage in the manufacturing of the dental implant, in accordance with some applications of the present invention.
Figure 3:
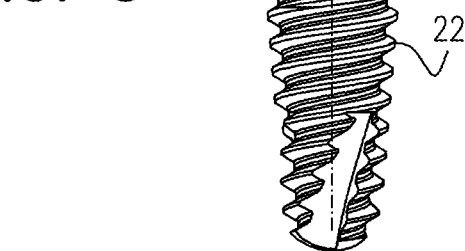

Reference is now made to FIGS. 2 and 3. Dental implant 20 is formed from a single metal piece 28 (shown in FIG. 2), e.g., from a cylindrical rod. Metal piece 28 is formed into dental implant 20 by shaping fixture 22 and customized emergence collar 24 from metal piece 28. Typically, metal piece 28 comprises titanium, or another suitable material.

In accordance with some applications of the present invention, fabrication of fixture 22 and customized emergence collar 24 is performed during two separate manufacturing procedures. Fabrication of fixture 22 is typically performed in a standardized manufacturing procedure (e.g., by machining), prior to fabrication of customized emergence collar 24. In other words, the bone-entry portion of implant 20, i.e., fixture 22, is pre-fabricated as a standard non-customized threaded fixture. Additionally, fixture 22 is typically treated in order to increase roughness of a surface of fixture 22 to maximize contact between the implant and the bone, improve stability, and enlarge implant surface area. (This treatment may be performed before or after the fabrication of customized emergence collar 24 described hereinbelow.)

FIGS. 2 and 3 show fixture 22 manufactured as a standard, non-customized threaded fixture. FIGS. 2 and 3 additionally show a blank portion 40 (the dimensions of which are not to scale), which is typically a portion of metal piece 28, blank portion 40 not yet having been machined, and disposed coronally to non-customized threaded fixture 22. Thus, typically, but not necessarily, blank portion 40 is cylindrical and has the same diameter D3 as metal piece 28. By contrast, fixture 22 is formed from the same metal piece 28, but due to the machining to create fixture 22, diameter D2 of fixture 22 is smaller than diameter D3 of blank portion 40.

For some applications, blank portion 40 is machined or otherwise shaped to provide a non-customized screw access hole 38 (e.g., as shown in FIG. 5), which is co-axial with longitudinal axis A1 of fixture 22 (FIG. 5). It is noted that for some applications, screw access hole 38 is customized based on the subject's CT and oral scan data.

In the transition from blank portion 40 shown in FIG. 2 to the customized emergence collar 24 shown in FIGS. 4 and 5, blank portion 40 typically undergoes machining into customized emergence collar 24 based on the subject's CT and oral scan data. When the subject's CT and oral scan data are received, and a design plan is created for customized emergence collar 24 that is suitable for the subject, customized emergence collar 24 is fabricated along blank portion 40. Customized emergence collar 24 is shaped and sized to facilitate suitable positioning of the dental crown over an abutment which is placed over customized emergence collar 24, and to facilitate improved gum healing and gum shaping. Thus, customized emergence collar 24 serves in effect as a healing abutment, although it is not removed from the subject to be replaced by a permanent abutment (as is the case with standard healing abutments). Rather, in accordance with some applications of the present invention, the permanent abutment is placed on customized emergence collar 24, and the dental crown is positioned on the permanent abutment in accordance with the customization of emergence collar 24. By not providing a step of removing a healing abutment and placing a permanent abutment, this application of the present invention reduces procedure time and enhances the ability of the subject's body to provide improved sealing of local tissue to the customized emergence collar.

For some applications, the surface treatment of fixture 22 is performed at the time of fabrication of customized emergence collar 24 from blank portion 40.

Figure 1:
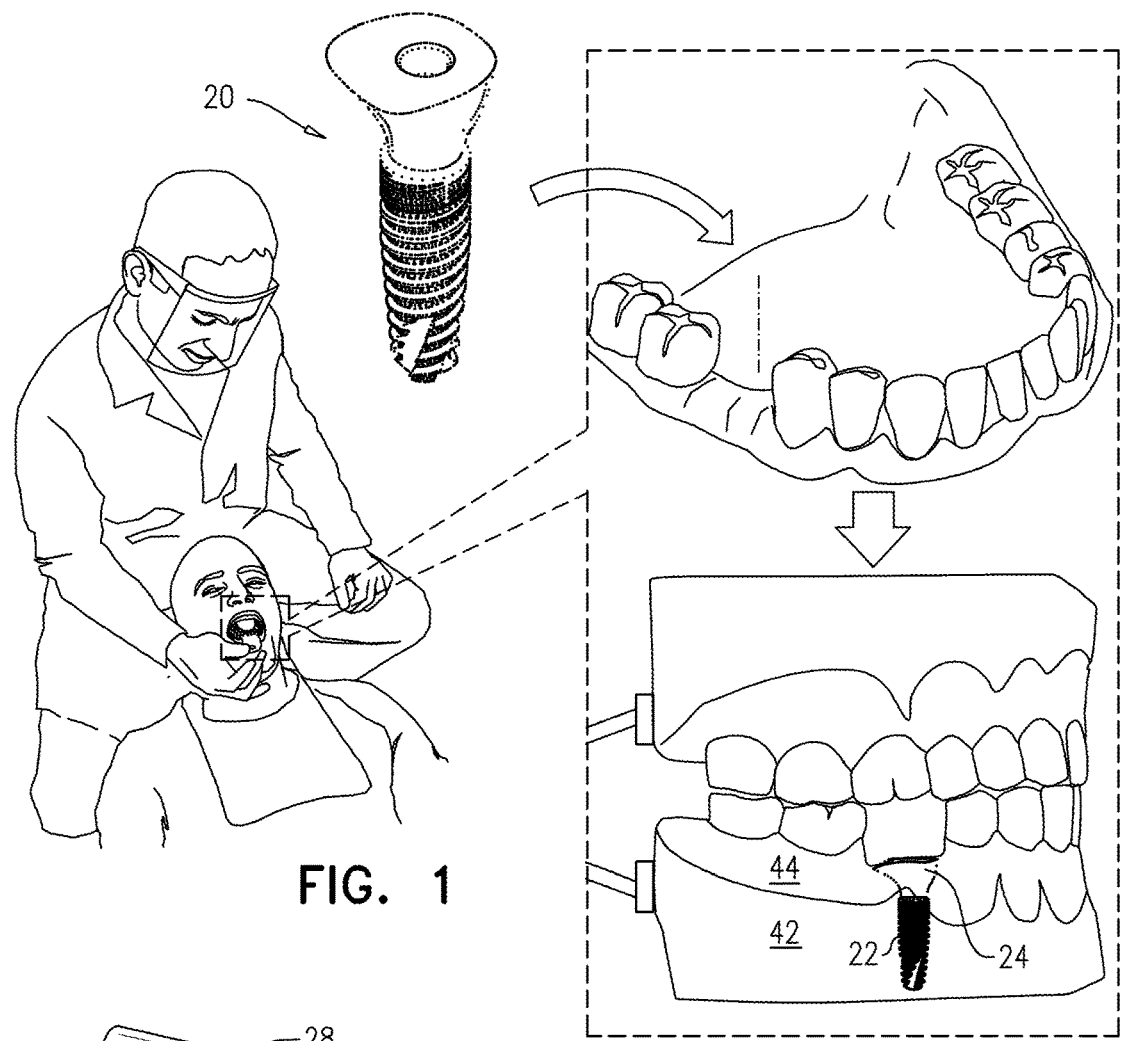
FIG. 1 is a schematic illustration of a subject undergoing implantation of a dental implant, in accordance with some applications of the present invention.
Figure 6A:
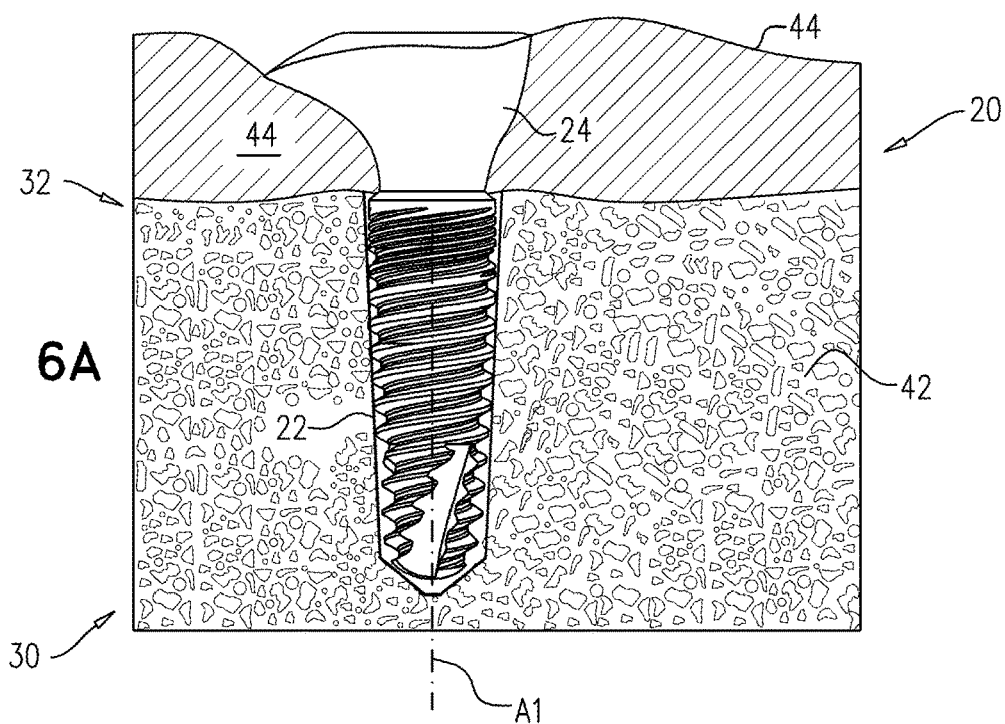
FIG. 6A is a schematic illustration of the dental implant, implanted in the subject, in accordance with some applications of the present invention.

Reference is now made to FIGS. 1 and 6A-C. FIGS. 1 and 6A are schematic illustrations of dental implant 20 implanted in a bone 42 of the subject. When dental implant 20 is implanted in the subject, fixture 22 is inserted into bone 42 and customized emergence collar 24 remains disposed in oral soft tissue, i.e., gum 44.

As shown in FIG. 6A, fixture 22 of implant 20 forms a bone-entry portion having central longitudinal axis A1 and having a coronal portion 32 and an apical portion 30. Hole 38 of customized emergence collar 24 is aligned with central longitudinal axis A1 in order to facilitate implantation of implant 20 using screw access hole 38 (shown in FIG. 5). Additionally, as shown, customized emergence collar 24 has a non-circular cross-section at least in a plane that is at least 1 millimeter coronal to fixture 22 and that is perpendicular to central longitudinal axis A1 of fixture 22.

Figure 6B:
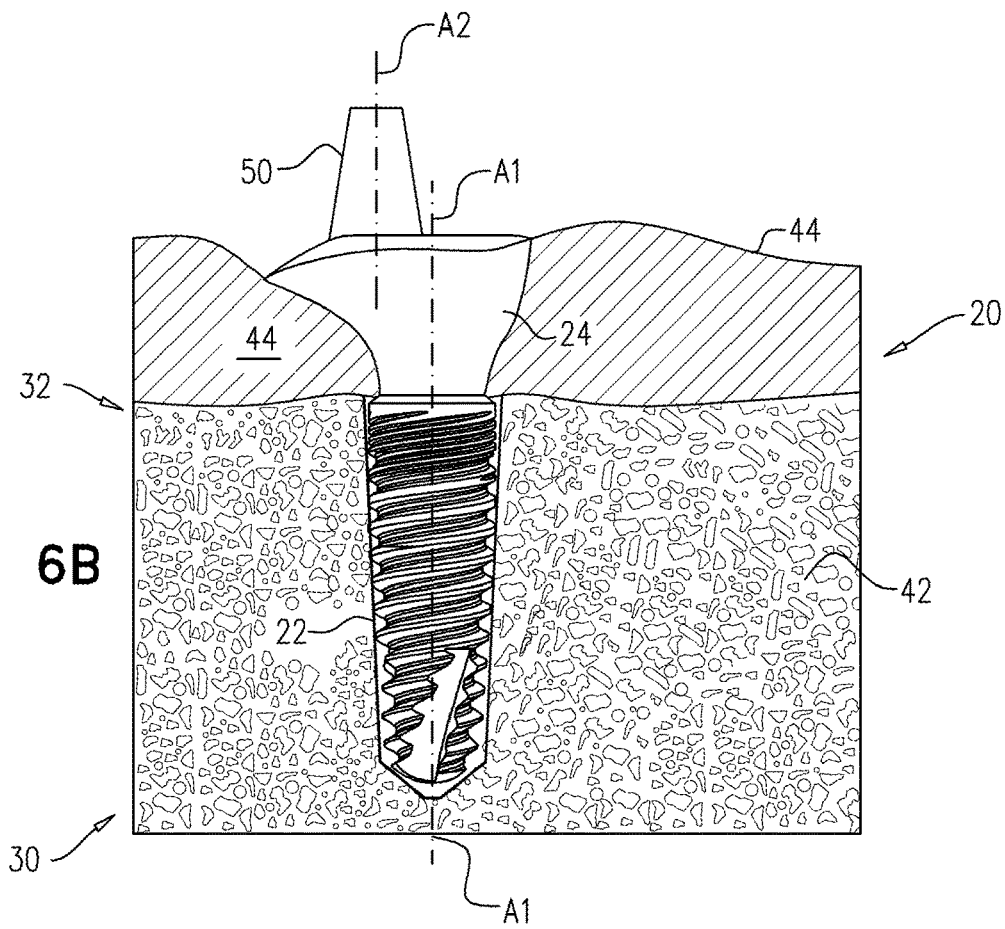
FIG. 6B is a schematic illustration of an abutment placed on the dental implant, implanted in the subject, in accordance with some applications of the present invention.

Reference is now made to FIG. 6B, which is a schematic illustration of an abutment 50 coupled to customized emergence collar 24 at an abutment-coupling surface 33 (FIG. 5) of customized emergence collar 24. As shown in FIG. 6B, abutment 50 is typically placed on customized emergence collar 24 such that a central longitudinal axis A2 of abutment 50 is not collinear with central longitudinal axis A1 of implant 20. Alternatively, for some applications, abutment 50 is placed on customized emergence collar 24 such that central longitudinal axis A2 of abutment 50 is collinear with central longitudinal axis A1 of implant 20. In general, abutment 50 is typically placed on customized emergence collar 24 at a distance of 0-5 mm from screw access hole 38. For some applications, abutment 50 is secured to customized emergence collar 24 by an intermediate holding piece, e.g., by a z-shaped tool analogous to a z-shaped hex (Allen™) key. (The angles of the "z" in this instance may be right angles.) Alternatively, or additionally, abutment 50 is secured to customized emergence collar 24 by a suitable adhesive.

Figure 6C:
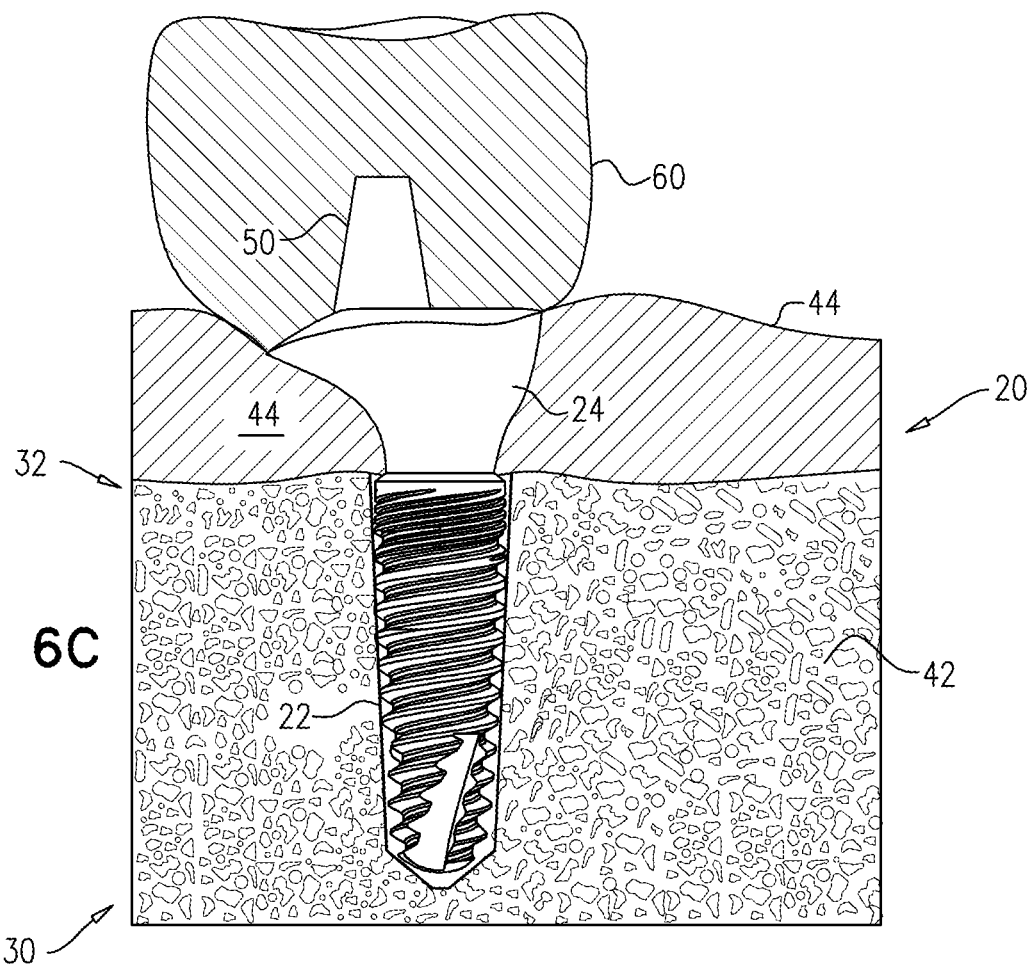
FIG. 6C is a schematic illustration of a dental crown placed on the abutment which is placed on the dental implant, implanted in the subject, in accordance with some applications of the present invention.

Reference is now made to FIG. 6C, which is a schematic illustration of a dental crown 60 placed on abutment 50 which is placed on customized emergence collar 24. As shown, use of customized emergence collar 24 allows customized positioning of dental crown 60 in such a way that it is not necessarily aligned with central longitudinal axis A1 of implant 20 (providing improved functional and esthetic results).

Reference is still made to FIG. 6C. Forming dental implant 20 from a single piece of metal, and shaping the single piece of metal into both fixture 22 and customized emergence collar 24, typically provides a smooth, generally seam-free transition between fixture 22 and customized emergence collar 24. Having a seam-free transition between fixture 22 and customized emergence collar 24 typically reduces bacterial leakage along the fixture-emergence collar interface. Bacterial leakage is known to occur along an implant fixture-abutment seam. This is known to occur due to cavities and gaps that form where an abutment is placed on an implanted fixture, in which the implanted fixture and abutment are separate components, in contrast to the dental implant 20 as provided by some applications of the present invention, which has no seam (as a seam would occur between two originally-separate components that have been attached). Such a seam is particularly a problem when an abutment is directly placed on a bone-level implant fixture, because the bacterial leakage along the fixture-abutment seam occurs in proximity to the bone. Bacterial leakage at the bone is known to result in damage to the bone.

In the case of implant 20, there is no seam between fixture 22 and emergence collar 24, and thus there is no seem at the bone level, thereby reducing the possibility of bacterial leakage at the bone. Furthermore, in the case of implant 20, the interface between customized emergence collar 24 and abutment 50 (and dental crown 60) is located at a soft tissue level (i.e., at gum 44), rather than at bone 42, thereby distancing the interface between implant 20 and abutment 50 from bone 42. Consequently, possible bacterial leakage is distanced from bone 42. Additionally, the subject at home and a caregiver in a dentist's office gain improved access to the interface between implant 20 and abutment 50 (and dental crown 60), thereby facilitating cleaning and oral hygiene.

It is noted that although data about the subject are described herein as being obtained using intra-oral scanning and/or CT scanning, the scope of the present invention includes other modalities for obtaining data about the subject in order to generate customized emergence collar 24.

Figure 7:
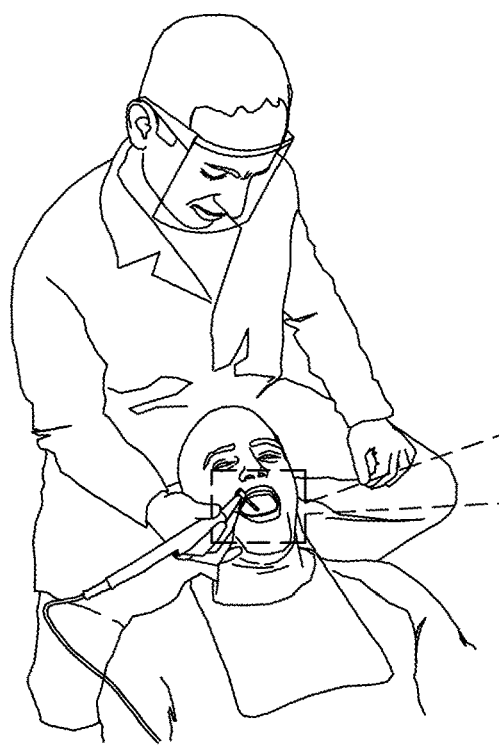
FIG. 7 is a schematic illustration of the dental implant being implanted in the subject, in accordance with some applications of the present invention.
Figure 7:
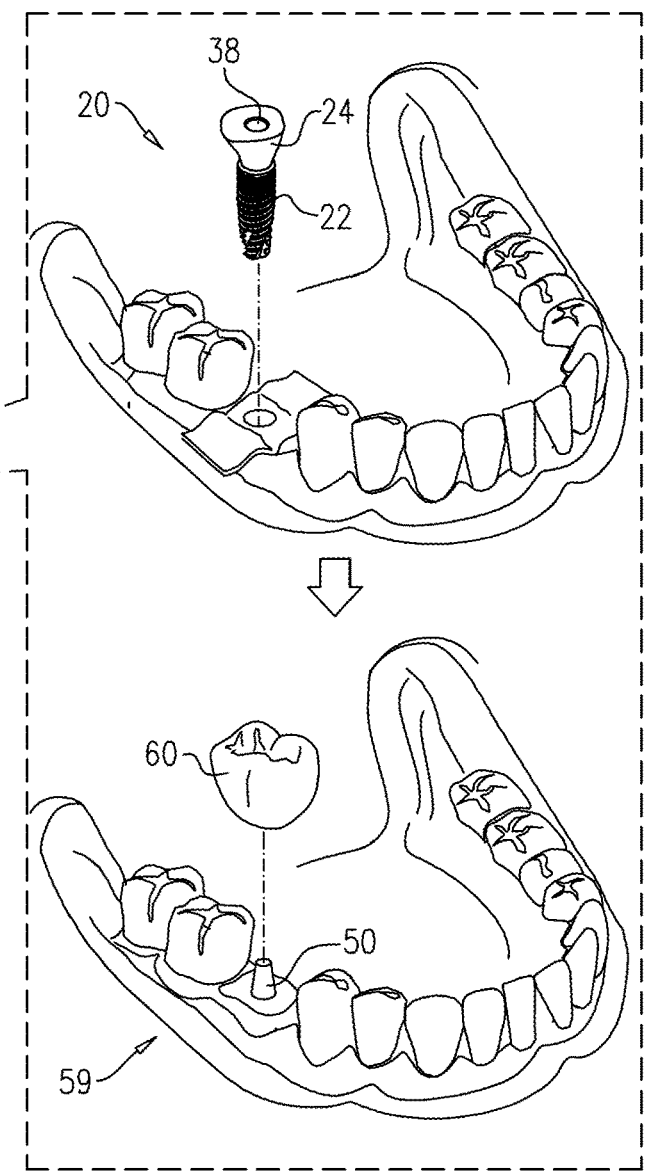
Figure 8:
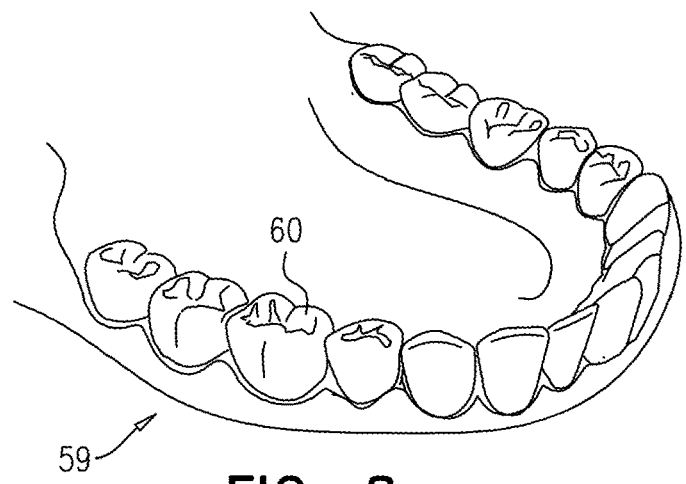
FIG. 8 is a schematic illustration of a dental arch of the subject following implantation of the dental implant, in accordance with some applications of the present invention.

Reference is now made to FIGS. 7 and 8. FIG. 7 is a schematic illustration of dental implant 20 being implanted in the subject, in accordance with some applications of the present invention. As shown, implant 20 is implanted such that fixture 22 is implanted in bone 42 of the subject, and customized emergence collar 24 is positioned in gums 44. Abutment 50 and dental crown 60 are then positioned on implant 20 during the same procedure or during one or more separate procedures.

FIG. 8 is a schematic illustration of a dental arch 59 of the subject following implantation of dental implant 20, in accordance with some applications of the present invention.

Embodiments of the present invention for creating the customized emergence collar described herein can take the form of an entirely hardware embodiment, an entirely software embodiment or an embodiment including both hardware and software elements. In an embodiment, the invention is implemented in software, which includes but is not limited to firmware, resident software, microcode, etc.

Furthermore, the embodiments of the invention can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Typically, the operations described herein to create the customized emergence collar are performed by a system that transforms the physical state of a memory, which is a real physical article, to have a different magnetic polarity, electrical charge, or the like depending on the technology of the memory that is used.

A data processing system suitable for storing and/or executing program code for creating the customized emergence collar will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read inventive instructions for creating the customized emergence collar on the program storage devices, and follow these instructions to execute the methodology of the embodiments of the invention.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Computer program code for carrying out operations of embodiments of the present invention may be written in any combination of one or more programming languages, including an object oriented programming language such as Java, Smalltalk, C++ or the like and conventional procedural programming languages, such as the C programming language or similar programming languages.

Computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified herein. These computer program instructions may also be stored in a computer-readable medium that can direct a computer or other programmable data processing apparatus to function in a particular manner, such that the instructions stored in the computer-readable medium produce an article of manufacture (e.g., the customized emergence collar). The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A dental implant having a central longitudinal axis at a bone-entry portion thereof, and comprising:
   a screw-threaded elongate fixture, at the bone-entry portion of the dental implant, shaped and sized for insertion into a bone of a subject, substantially the entire length of the bone-entry portion being screw-threaded; and
   a non-threaded emergence collar emerging from the fixture and coronal to the fixture, the entirety of the emergence collar being smooth, the emergence collar having a non-circular cross-section at least in a plane that is at least 1 millimeter coronal to the fixture and that is perpendicular to the longitudinal axis, and the emergence collar and the fixture being formed of, and adjacently disposed along, a single piece of metal.

2. The dental implant according to claim 1, wherein the emergence collar is formed by using intra-oral scan and CT scan data of the subject, and wherein the emergence collar is shaped and sized for insertion into oral soft tissue of the subject based on the scan data.

3. The dental implant according to claim 1, further comprising an abutment configured to be coupled to the emergence collar such that a central longitudinal axis of the abutment is not collinear with the central longitudinal axis of the dental implant.

4. The dental implant according to claim 3, further comprising a dental crown configured to be coupled to the abutment.

5. The dental implant according to claim 1 wherein the fixture has a length of 6-20 mm.

6. The dental implant according to claim 1, wherein the fixture has a diameter at a largest threaded portion of the fixture that is 2-9 mm.

7. A method for generating a dental implant having a fixture and an emergence collar, the method comprising:
   receiving a fixture as a non-customized screw-threaded fixture, a blank portion being disposed coronally to the non-customized screw-threaded fixture, the non-customized screw-threaded fixture and the blank portion being a single piece of metal;
   receiving data from a CT scan and an intra-oral scan of a subject; and
   forming, along the blank portion, a non-threaded emergence collar based on the CT and intra-oral scan data, the emergence collar (a) being entirely smooth, (b) emerging from and disposed coronal to the fixture of the dental implant, (c) having a circular cross-section at an apical end of the emergence collar, and (d) having a non-circular cross-section at least in a plane that is at least 1 millimeter coronal to the fixture and that is perpendicular to the longitudinal axis.

8. The method according to claim 7, wherein receiving the fixture comprises receiving the fixture prior to receiving the data.

9. The method according to claim 7, further comprising implanting the dental implant in a subject's mouth such that the fixture is positioned in bone and the emergence collar is positioned in soft tissue of the subject.

10. The method according to claim 9, further comprising placing an abutment on the emergence collar such that a central longitudinal axis of the abutment is not collinear with a central longitudinal axis of the dental implant.

11. The method according to claim 10, further comprising placing a dental crown on the abutment.

12. The method according to claim 10, wherein placing the abutment does not comprise providing a step of removing a healing abutment and placing a permanent abutment.

13. The method according to claim 10, wherein placing the abutment comprises placing the abutment such that the interface between the emergence collar and the abutment is located at a soft tissue level.

* * * * *